United States Patent
Ray

(10) Patent No.: US 9,822,314 B2
(45) Date of Patent: Nov. 21, 2017

(54) PROCESSES FOR PRODUCING FUELS FROM A RENEWABLE FEED

(71) Applicant: UOP LLC, Des Plaines (IL)

(72) Inventor: Anjan Ray, New Delhi (IN)

(73) Assignee: UOP LLC, Des Plaines, IL (US)

( * ) Notice: Subject to any disclaimer, the term of this patent is extended or adjusted under 35 U.S.C. 154(b) by 322 days.

(21) Appl. No.: 14/678,268

(22) Filed: Apr. 3, 2015

(65) Prior Publication Data

US 2016/0289570 A1    Oct. 6, 2016

(51) Int. Cl.
| | | |
|---|---|---|
| C10G 45/58 | (2006.01) |
| C11C 3/14 | (2006.01) |
| C10G 3/00 | (2006.01) |
| C10L 1/04 | (2006.01) |
| C07C 5/27 | (2006.01) |
| C11C 3/12 | (2006.01) |
| C10L 1/06 | (2006.01) |
| C10L 1/08 | (2006.01) |

(52) U.S. Cl.
CPC .............. *C10G 3/50* (2013.01); *C07C 5/2767* (2013.01); *C10G 3/42* (2013.01); *C10G 45/58* (2013.01); *C10L 1/04* (2013.01); *C10L 1/06* (2013.01); *C10L 1/08* (2013.01); *C11C 3/12* (2013.01); *C10G 2300/1011* (2013.01); *Y02E 50/13* (2013.01); *Y02P 30/20* (2015.11); *Y02T 50/678* (2013.01)

(58) Field of Classification Search
None
See application file for complete search history.

(56) References Cited

U.S. PATENT DOCUMENTS

| | | | |
|---|---|---|---|
| 8,865,953 B2 | 10/2014 | Brady et al. |
| 8,865,954 B2 | 10/2014 | Kalnes et al. |
| 8,927,795 B2 | 1/2015 | McCall et al. |
| 2004/0230085 A1 * | 11/2004 | Jakkula ............... C10G 3/45 585/240 |

FOREIGN PATENT DOCUMENTS

| | | |
|---|---|---|
| WO | WO 2009/039000 A3 | 3/2009 |
| WO | WO 2014/001633 A1 | 1/2014 |

OTHER PUBLICATIONS

Santana et al., "Trans-free hydrogenation of vegetable fat in vapor fase supercritical modified CO2," AIChE Annual Meeting (2008), Conference Proceedings, 10 pages.

* cited by examiner

*Primary Examiner* — Tam M Nguyen

(57) ABSTRACT

Processes for the production of hydrocarbons from a renewable feedstock in which the renewable feedstock is partially hydrogenated prior to being deoxygenated. The partially hydrogenation utilizes a lower pressure, lower purity or both hydrogen gas compared to the deoxygenation. The partially hydrogenated product may be stored in containers and transported to be deoxygenated. Prior to partially hydrogenation, the feedstock may be pretreated. After deoxygenation an isomerization zone may be used to increase the cold flow properties for a diesel fuel.

17 Claims, 1 Drawing Sheet

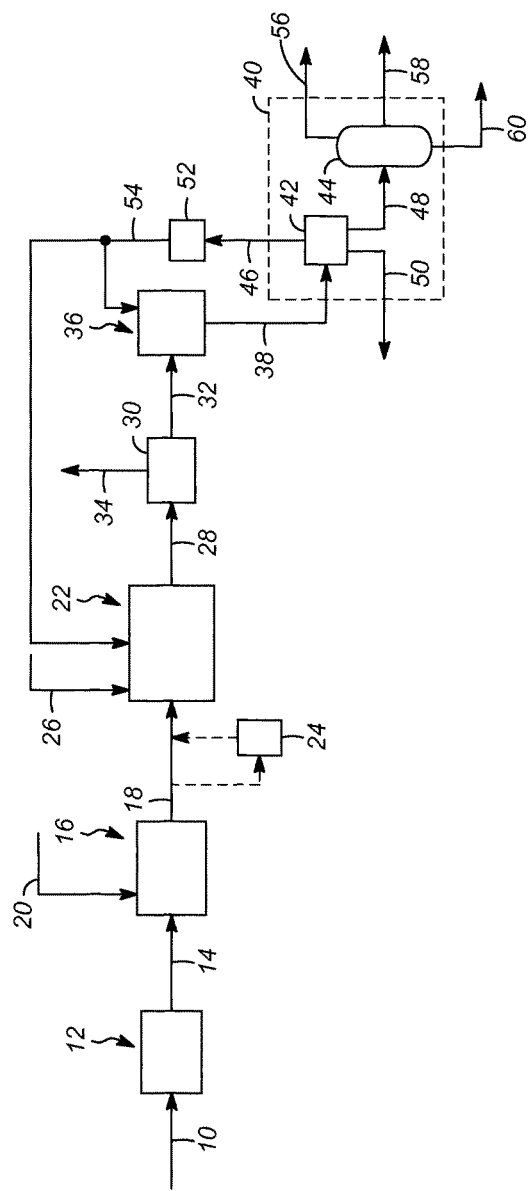

PROCESSES FOR PRODUCING FUELS FROM A RENEWABLE FEED

FIELD OF THE INVENTION

The present invention relates to processes for producing hydrocarbons useful as diesel boiling range fuel or aviation range fuel components from renewable feedstocks such as triglycerides and free fatty acids found in materials such as plant and animal fats and oils. More specifically, the present invention relates to such processes that partially hydrogenate the renewable feedstocks before converting triglycerides and free fatty acids into long chain hydrocarbons.

BACKGROUND OF THE INVENTION

As the demand for fuel increases worldwide, there is increasing interest in producing fuels and blending components from sources other than crude oil. Often referred to as a renewable source, these sources include, but are not limited to, plant oils such as corn, rapeseed, canola, soybean, microbial oils such as algal oils, animal fats such as inedible tallow, fish oils and various waste streams such as yellow and brown greases and sewage sludge. A common feature of these sources is that they are composed of glycerides and Free Fatty Acids (FFA). Both triglycerides and the FFAs contain aliphatic carbon chains having from about 8 to about 24 carbon atoms. The aliphatic carbon chains in triglycerides or FFAs can be fully saturated, or mono, di or poly-unsaturated.

U.S. Pat. No. 4,300,009 discloses the use of crystalline aluminosilicate zeolites to convert plant oils, such as corn oil, to hydrocarbons for use as gasoline and chemicals such as para-xylene. U.S. Pat. No. 4,992,605 discloses the production of hydrocarbon products in the diesel boiling range by hydroprocessing vegetable oils such as canola or sunflower oil. Finally, US 2004/0230085 A1 discloses a process for treating a hydrocarbon component of biological origin by hydrodeoxygenation followed by isomerization.

Applicant has developed a process which comprises one or more steps to hydrogenate and deoxygenate (via catalytic decarboxylation, decarbonylation and/or hydrodeoxygenation) and isomerize the feedstock. The effluent from the isomerization zone is separated into at least a vapor portion and a liquid portion comprising hydrocarbons that can used as a fuel, such as a diesel range or aviation range fuel.

Impurities in such feedstock fats and oils, such as feedstocks derived from plant, animal or microbe (bacteria, algae, fungi), result in increased capital spend, higher operating expenditure, and reduced net yields of products. Such feedstock often require pretreatment (such as with mineral acids or with ion exchange resins) to remove contaminants such as phosphorus, nitrogen and metals. While the pretreatment may remove the contaminants, up to 5% of feedstock may be lost in the pretreatment processing steps. Since the feedstock cost can represent a significant portion of the production cost, even a small loss of feedstocks can impact on operating cost. Additionally, as a result of the contaminants, a guard bed is typically required to protect the more expensive downstream catalysts for the deoxygenation and isomerization steps. The guard bed may increase capital cost and operating cost, and may also potentially reduce the number of operating days in a year due to guard bed maintenance and adsorbent change. Furthermore, the current processes typically utilize hydrogen which is high purity (99.9% hydrogen) and has a high pressure (greater than 2 MPa). Hydrogen or hydrogen production feedstock such as natural gas availability in certain areas may be low, making the cost and use of hydrogen an important factor for many refiners. Finally, some feedstocks contain polyunsaturated lipids (such as those derived from fish oil, salicornia or certain algae) which have a reduced shelf life due to oxidation stability issues.

Therefore, it would be desirable to provide processes for the production of hydrocarbons from a renewable feedstock which can lower the amount of high purity and high pressure hydrogen required.

Additionally, it would be desirable to provide processes for the production of hydrocarbons from a renewable feedstock which increase the shelf life of the feedstocks allowing for more efficient batch production.

SUMMARY OF THE INVENTION

One or more processes for the production of hydrocarbons from a renewable feedstock have been invented.

In a first aspect of the invention, the present invention may be broadly characterized as a providing a process for producing a transportation fuel from a renewable feedstock by: pretreating the feedstock in a first pretreatment zone to provide a pretreated feedstock; pre-hydrogenating the pretreated feedstock in a pre-hydrogenation zone, the pre-hydrogenation zone comprising at least one reactor having a hydrogenation catalyst and being operated under conditions to partially hydrogenate the pretreated feedstock to provide a pre-hydrogenated feedstock; deoxygenating the pre-hydrogenated feedstock in a deoxygenation zone, the deoxygenation zone comprising at least one reactor having a catalyst capable of deoxygenating the pre-hydrogenated feedstock under deoxygenation conditions and providing a deoxygenated effluent; and, separating at least one transportation fuel stream from the deoxygenated effluent. Both the pre-hydrogenation zone and the deoxygenation zone receive a hydrogen gas stream, and the hydrogen gas stream received by the pre-hydrogenation zone has a lower purity, a lower pressure or both compared to the hydrogen gas stream received by the deoxygenation zone.

In some embodiments of the present invention, the hydrogen gas stream received by the pre-hydrogenation zone has a lower purity and a lower pressure compared to the hydrogen gas stream received by the deoxygenation zone.

In at least one embodiment of the present invention, the pressure of the hydrogen gas stream received by the deoxygenation zone is at least 2 MPa.

In various embodiments of the present invention, the purity of the hydrogen gas stream received by the deoxygenation zone is at least 90%.

In some embodiments of the present invention, the process further includes isomerizing the deoxygenated effluent in an isomerization zone. The isomerization zone may comprise a reactor having a catalyst capable of isomerizing at least a portion of the deoxygenated effluent to provide an isomerized effluent. It is contemplated that the reactor in the isomerization zone and the reactor in the deoxygenating zone are the same.

In various embodiments of the present invention, the process further includes storing the pre-hydrogenated feedstock in containers. It is contemplated that the process also includes transporting the containers of the pre-hydrogenated feedstock to the deoxygenation zone.

In one or more embodiments of the present invention, the process includes removing contaminants from the pre-hydrogenated feedstock in a guard bed prior to deoxygenating the pre-hydrogenated feedstock in the deoxygenation zone.

In a second aspect of the present invention, the invention may be broadly characterized as providing a process for producing a transportation fuel from a renewable feedstock by: passing a renewable feedstock to a first pretreatment zone, the pretreatment zone comprising at least one reactor configured to degum the renewable feedstock, bleach the renewable feedstock, polish the renewable feedstock or a combination thereof, to provide a pretreated feedstock; passing the pretreated feedstock to a pre-hydrogenation zone, the pre-hydrogenation zone comprising at least one reactor having a hydrogenation catalyst and being operated under conditions to partially hydrogenate, in the presence of hydrogen, the pretreated feedstock to provide a pre-hydrogenated feedstock; passing a first hydrogen containing gas to the pre-hydrogenation zone, the first hydrogen containing gas having a first pressure and a first purity; passing the pre-hydrogenated feedstock to a deoxygenation zone, the deoxygenation zone comprising at least one reactor having a catalyst capable of deoxygenating, in the presence of hydrogen, the pre-hydrogenated feedstock under deoxygenation conditions to provide a deoxygenated effluent; and, passing a second hydrogen containing gas to the deoxygenation zone, the second hydrogen containing gas having a second pressure and a second purity. The second pressure is at least 2 MPa bar, and at least one of the second pressure and the first pressure, and the first purity and the second purity are different.

In some embodiments of the present invention, the process includes separating at least one transportation fuel stream from the deoxygenated effluent.

In at least one embodiment of the present invention, the process also includes isomerizing the deoxygenated effluent in an isomerization zone, the isomerization zone comprising a reactor having a catalyst capable of isomerizing at least a portion of the deoxygenated effluent to provide a isomerized effluent, and separating at least one transportation fuel stream from the isomerized effluent.

In some embodiments of the present invention, the first pressure is lower than the second pressure and the first purity is less that the second purity. It is contemplated that the second purity is greater than 90%.

In one or more embodiments of the present invention, the process also includes storing the pre-hydrogenated feedstock in one or more containers prior to passing the pre-hydrogenated feedstock to the deoxygenation zone.

In various embodiments of the present invention, the pre-hydrogenated feedstock is passed to the deoxygenation zone without passing through a guard bed.

In at least one embodiment of the present invention, the process includes removing contaminants from the pre-hydrogenated feedstock in a guard bed prior to deoxygenating the pre-hydrogenated feedstock in the deoxygenation zone.

In some embodiments of the present invention, the pre-hydrogenated feedstock is rich in saturated oils.

In various embodiments of the present invention, the process also includes removing phosphorus from the pretreated feedstock in the pre-hydrogenation zone.

In one or more embodiments of the present invention, the process includes passing the deoxygenated effluent to a separation zone having a separation vessel and a fractionation column, separating the deoxygenated effluent into liquid hydrocarbon stream and a vapor hydrocarbon stream in the separation vessel and, separating the liquid hydrocarbon stream into a light hydrocarbon stream, a naphtha stream and a diesel stream.

Additional aspects, embodiments, and details of the invention, which may be combined in any manner, are set forth in the following detailed description of the invention.

DETAILED DESCRIPTION OF THE DRAWINGS

One or more exemplary embodiments of the present invention will be described below in conjunction with the following drawing FIGURE, in which:

the FIGURE shows a process flow diagram of one or more processes according to the present invention.

DETAILED DESCRIPTION OF THE INVENTION

As mentioned above, one or more processes for the production of hydrocarbons from a renewable feedstock have been invented. In the various processes of the present invention, a renewable feedstock is partially hydrogenated before undergoing deoxygenation. The partial hydrogenation will lower the amount of high purity/high pressure hydrogen utilized for the deoxygenation and isomerization. Additionally, the partially hydrogenated feedstock will have a longer shelf life and may be stored, or transported to another refinery. Further, the partially hydrogenation may lessen the need for a guard bed before the deoxygenation and may allow for downstream equipment and vessels to be made from different, less expensive metals.

With these general principles in mind, one or more embodiments of the present invention will be described with the understanding that the following description is not intended to be limiting.

Turning to FIG. 1, the various embodiments of the present invention relate to a process for producing a hydrocarbon stream, useful as diesel boiling range fuel for example, from a renewable feedstock 10 such as renewable feedstocks originating from plants or animals. Some of these renewable feedstocks are known as biorenewable fats and oils. The term "renewable feedstock" is meant to include feedstocks other than those obtained from crude oil. The renewable feedstock 10 may include any of those feedstocks which comprise at least one of glycerides and free fatty acids (FFA). Most of triglycerides will be triglycerides, but monoglycerides and diglycerides may be present and processed as well. Examples of these renewable feedstocks include, but are not limited to, canola oil, corn oil, soy oils, rapeseed oil, soybean oil, colza oil, tall oil, sunflower oil, hempseed oil, olive oil, linseed oil, coconut oil, castor oil, peanut oil, palm oil, mustard oil, tallow, yellow and brown greases, lard, train oil, fats in milk, fish oil, algal oil, sewage sludge, and the like. Additional examples of renewable feedstocks include non-edible vegetable oils from the group comprising *Jatropha curcas* (Ratanjot, Wild Castor, Jangli Erandi), *Madhuca indica* (Mohuwa), *Pongamia pinnata* (Karanji, Honge), *calophyllum inophyllum, moringa oleifera* and *Azadirachta indica* (Neem). The triglycerides and FFAs of the typical vegetable or animal fat contain aliphatic hydrocarbon chains in their structure which have about 8 to about 30 carbon atoms. As will be appreciated, the renewable feedstock may comprise a mixture of one or more of the foregoing examples.

The renewable feedstocks 10 that can be used in the present invention may contain a variety of impurities. For example, tall oil is a byproduct of the wood processing industry and tall oil contains esters and rosin acids in addition to FFAs. Rosin acids are cyclic carboxylic acids. The renewable feedstocks 10 may also contain contaminants such as alkali metals, e.g. sodium and potassium, phosphorous as well as solids, water and detergents. Therefore, an optional first step is to remove as much of these contaminants as possible in a pretreatment zone 12 to provide a pretreated feedstock 14.

The pretreatment zone 12 may comprise, for example, an ion-exchange resin at pretreatment conditions. The ion-exchange resin may be an acidic ion exchange resin such as Amberlyst™-15 and can be used as a bed in a reactor through which the renewable feedstock 10 is flowed through, either upflow or downflow. Conditions at which the ion-exchange resin in the pretreatment zone 12 is operated are well known in the art. The pretreatment zone 12 may comprise a mild acid wash. This is carried out by contacting the renewable feedstock 10 with an acid such as sulfuric, nitric or hydrochloric acid in a reactor. The acid and the renewable feedstock 10 may be contacted either in a batch or continuous process. Contacting may be done with a dilute acid solution usually at ambient temperature and atmospheric pressure. If the contacting is done in a continuous manner, it is usually done in a counter-current manner. The pretreatment zone 12 may comprise a guard bed to remove metal contaminants from the renewable feedstock 10 which is well known in the art. These can include alumina guard beds either with or without demetallation catalysts such as nickel or cobalt. Filtration and solvent extraction techniques are other choices which may be employed in such a guard bed. Additionally, the pretreatment zone 12 may comprise a zone which at least one reactor configured to degum the renewable feedstock, bleach the renewable feedstock, polish the renewable feedstock or a combination thereof. See, *Developments in Edible Oil Refining for the Production of High Quality Food Oils*, Wim de Greyt, 101$^{st}$ AOCS Annual Meeting, May 16-19, 2010, Phoenix, Ariz. US. It should be appreciated that the pretreatment zone may utilize one or more of the aforementioned treatment processes, or any other equipment or processes that is designed to remove one or more contaminants or improve one or more qualities of the renewable feedstocks 10.

Returning to the FIGURE, after the pretreatment zone 12, the pretreated feedstock 14 is pre-hydrogenated in a pre-hydrogenation zone 16 to provide a pre-hydrogenated feedstock 18. The pretreatment zone 12 and the pre-hydrogenation zone 16 may not be located in the same refinery (i.e., instead of passing the pretreated feedstock 14 from the pretreatment zone 12 to the pre-hydrogenation zone 16 via lines or process piping, the pretreated feedstock 14 may be stored and transported to the pre-hydrogenation zone 16 in various containers, such as barrels).

The pre-hydrogenation zone 16 may comprise at least one reactor having a hydrogenation catalyst and being operated under conditions to partially hydrogenate the pretreated feedstock 14 to provide the pre-hydrogenated feedstock 18. Hydrogenation catalysts are any of those well known in the art such as nickel or nickel/molybdenum dispersed on a high surface area support. Other hydrogenation catalysts include one or more noble metal catalytic elements dispersed on a high surface area support. Other hydrogenation catalysts include one or more noble metal catalytic elements dispersed on a high surface area support. Non-limiting examples of noble metals include Pt and/or Pd dispersed on, for example, gamma-alumina.

The pre-hydrogenation zone 16 also receives a hydrogen gas 20. However, the hydrogen gas 20 may be a low pressure (in some embodiments, less than 3 MPa, in yet other embodiments less than 2 MPa, and in still other embodiments, less than 0.1 MPa) and low purity (in some embodiments, greater than 50% and less than 99.9% hydrogen, in other embodiments, greater than 90% and less than 99.9% hydrogen) hydrogen gas 20.

Typical operating parameters for the pre-hydrogenation zone 16 comprise a pressure of 0.1 to 2.0 MPa and a temperature of between about 90 to about 180° C.

In the pre-hydrogenation zone 16, the unsaturated carbon-to-carbon bonds in the triglycerides and the FFAs will be saturated by the hydrogen in the hydrogen gas 20. Additionally, contaminants such as phosphorus may be significantly removed from the feedstock unsaturated oils. By "significantly removed" it is meant that at least 50% of the phosphorous is removed.

With the double bonds saturated, the pre-hydrogenated feedstock 18 will be rich in saturated oils (also referred to as saturated fats) and thus more stable. The pre-hydrogenated feedstock 18 will have a longer shelf compared to pretreated feedstocks that have not been partially hydrogenated. This allows for the pre-hydrogenated feedstock 18 to be stored and thus it can be transported to another refinery via containers without as much loss due to oxidation and agglomeration.

Whether being passed via process piping or other conduits, or passed via containers, the pre-hydrogenated feedstock 18 may be converted to hydrocarbons in a deoxygenation zone 22 comprising one or more catalyst beds in one or more reactors. Contaminants may optionally be removed from the pre-hydrogenated feedstock 18 in a guard bed 24 prior to converting the pre-hydrogenated feedstock 18 to hydrocarbons in the deoxygenation zone 22; however, due to the pre-hydrogenation, the use of the guard bed 24 may not be required. The guard bed 24 may comprise a vessel having one or more beds of sacrificial adsorbent capable of retaining undesired contaminants. Compared to processing streams that have not been pre-hydrogenation, the size of the guard bed 24 should be reduced, and the life of the adsorbent in same should be extended due to the lower level of contaminants flowing there through.

In the deoxygenation zone 22, the pre-hydrogenated feedstock 18 is contacted with a catalyst in the presence of hydrogen at deoxygenation conditions to deoxygenate the pre-hydrogenated feedstock 18. Deoxygenation reactions, including decarbonylation, decarboxylation, hydrodeoxygenation and deoxygenation, result in oxygen being removed. In order to provide hydrogen for these reactions, the deoxygenation zone 22 receives a hydrogen containing gas 26. Typically, the hydrogen containing gas 26 is a high pressure and high purity hydrogen gas, meaning the hydrogen containing gas 26 passed to the deoxygenation zone 22 comprises at least 99% hydrogen, preferably 99.9% hydrogen and has a pressure greater than 2 MPa. In addition to deoxygenation, any remaining olefinic or unsaturated portions of the n-paraffinic chains may be hydrogenated in the deoxygenation zone 22.

As mentioned above, in addition to hydrogen, the deoxygenation zone 22 includes a suitable catalysts which comprises any of those well known in the art such as nickel or nickel/molybdenum dispersed on a high surface area support. Other catalysts include one or more noble metal catalytic elements dispersed on a high surface area support. Non-limiting examples of noble metals include Pt and/or Pd dispersed on gamma-alumina.

Generally, deoxygenation conditions include a temperature of about 40 to about 700° C. and a pressure of about 700 kPa (100 psig) to about 21 MPa (3000 psig). Other operating conditions for the deoxygenation zone are well known in the art.

A reaction effluent 28 from the deoxygenation zone 22 may be separated in a separation vessel 30 into a liquid and a gaseous portion 34. The liquid portion 32 comprises a hydrocarbon fraction which is primarily paraffins (typically no more than 5 or 10 mass-% branched paraffins) and having a large concentration of paraffins in the range of C9 to C18 hydrocarbons. Different feedstocks will result in different distributions of paraffins. The gaseous portion 34 may comprise hydrogen, carbon dioxide, carbon monoxide, water vapor, propane, at least one sulfur component such as hydrogen sulfide, and a phosphorous component such as phosphine. The further processing of this stream is not necessary for an understanding or practicing of the present invention.

While a desired product, such as a transportation fuel, may be separated from the liquid portion 32 because the liquid portion 32 comprises mostly normal paraffins, it will have poor cold flow properties. Accordingly, to improve the cold flow properties of the liquid portion 32, it is preferred that at least the liquid portion 32 is contacted with an isomerization catalyst in an isomerization zone 36 under isomerization conditions to at least partially isomerize the normal paraffins to branched paraffins. Isomerization can be carried out in a separate bed of the deoxygenation zone 22, i.e. in the same reactor, or the isomerization can be carried out in a separate reactor. As will be appreciated, if the isomerization zone 36 and the deoxygenation zone 22 are disposed within the same reactor there is no need for a separation of the reaction effluent 28 from the deoxygenation zone 22. Additionally, even if the isomerization zone 36 and the deoxygenation zone 22 are in separate reactors, it is contemplated that the entire is reaction effluent 28 from the deoxygenation zone 22 is passed to the isomerization zone 36. For ease of description the following will address the embodiment where a different reactor is employed for the isomerization reaction.

The isomerization of the normal hydrocarbons can be accomplished in any manner known in the art or by using any suitable catalyst known in the art. One or more beds of catalyst may be used and the isomerization may be operated in a co-current mode of operation. Fixed bed, trickle bed down flow or fixed bed liquid filled up-flow modes are both suitable.

Suitable catalysts may comprise a metal of Group VIII (IUPAC 8-10) of the Periodic Table and a support material. Suitable Group VIII metals include platinum and palladium, each of which may be used alone or in combination. The support material may be amorphous or crystalline. Suitable support materials include amorphous alumina, amorphous silica-alumina, ferrierite, ALPO-31, SAPO-11, SAPO-31, SAPO-37, SAPO-41, SM-3, MgAPSO-31, FU-9, NU-10, NU-23, ZSM-12, ZSM-22, ZSM-23, ZSM-35, ZSM-48, ZSM-50, ZSM-57, MeAPO-11, MeAPO-31, MeAPO-41, MgAPSO-11, MgAPSO-31, MgAPSO-41, MgAPSO-46, ELAPO-11, ELAPO-31, ELAPO-41, ELAPSO-11, ELAPSO-31, ELAPSO-41, laumontite, cancrinite, offretite, hydrogen form of stillbite, magnesium or calcium form of mordenite, and magnesium or calcium form of partheite, each of which may be used alone or in combination. ALPO-31 is described in U.S. Pat. No. 4,310,440. SAPO-11, SAPO-31, SAPO-37, and SAPO-41 are described in U.S. Pat. No. 4,440,871. SM-3 is described in U.S. Pat. No. 4,943,424; U.S. Pat. No. 5,087,347; U.S. Pat. No. 5,158,665; and U.S. Pat. No. 5,208,005. MgAPSO is a MeAPSO, which is an acronym for a metal aluminumsilicophosphate molecular sieve, where the metal Me is magnesium (Mg). Suitable MgAPSO-31 catalysts include MgAPSO-31. MeAPSOs are described in U.S. Pat. No. 4,793,984, and MgAPSOs are described in U.S. Pat. No. 4,758,419. MgAPSO-31 is a preferred MgAPSO, where 31 means a MgAPSO having structure type 31. Many natural zeolites, such as ferrierite, that have an initially reduced pore size can be converted to forms suitable for olefin skeletal isomerization by removing associated alkali metal or alkaline earth metal by ammonium ion exchange and calcination to produce the substantially hydrogen form, as taught in U.S. Pat. No. 4,795,623 and U.S. Pat. No. 4,924,027. Further catalysts and conditions for skeletal isomerization are disclosed in U.S. Pat. No. 5,510,306, U.S. Pat. No. 5,082,956, and U.S. Pat. No. 5,741,759. The isomerization catalyst may also comprise a modifier selected from the group consisting of lanthanum, cerium, praseodymium, neodymium, samarium, gadolinium, terbium, and mixtures thereof, as described in U.S. Pat. No. 5,716,897 and U.S. Pat. No. 5,851,949. Other suitable support materials include ZSM-22, ZSM-23, and ZSM-35, which are described for use in dewaxing in U.S. Pat. No. 5,246,566 and in the article entitled "New Molecular Sieve Process for Lube Dewaxing by Wax Isomerization," written by S. J. Miller, in Microporous Materials 2 (1994) 439-449. U.S. Pat. No. 5,444,032 and U.S. Pat. No. 5,608,968 teach a suitable bifunctional catalyst which is constituted by an amorphous silica-alumina gel and one or more metals belonging to Group VIIIA, and is effective in the hydroisomerization of long-chain normal paraffins containing more than 15 carbon atoms. U.S. Pat. No. 5,981,419 and U.S. Pat. No. 5,908,134 teach a suitable bifunctional catalyst which comprises: (a) a porous crystalline material isostructural with beta-zeolite selected from boro-silicate (BOR—B) and boro-alumino-silicate (Al—BOR—B) in which the molar $SiO_2:Al_2O_3$ ratio is higher than 300:1; (b) one or more metal(s) belonging to Group VIIIA, selected from platinum and palladium, in an amount comprised within the range of from 0.05 to 5% by weight. Article V. Calemma et al., App. Catal. A: Gen., 190 (2000), 207 teaches yet another suitable catalyst. In sum, the isomerization catalyst may be any of those well known in the art such as those described and cited above.

Isomerization conditions generally include a temperature of about 150° C. to about 360° C. and a pressure of about 1724 kPa absolute (250 psia) to about 4726 kPa absolute (700 psia). In another embodiment, the isomerization conditions include a temperature of about 300° C. to about 360° C. and a pressure of about 3102 kPa absolute (450 psia) to about 3792 kPa absolute (550 psia). Other operating conditions for the isomerization zone 36 are well known in the art.

An isomerized effluent 38 from the isomerization zone 36 is a branched-paraffin-rich stream. By the term "rich" it is meant that the effluent stream has a greater concentration of branched paraffins than the stream entering the isomerization zone 36, and preferably comprises greater than 50 mass-% branched paraffins. It is envisioned that the isomerized effluent 38 may contain 70, 80, or 90 mass-% branched paraffins. Only minimal branching is required, enough to overcome the cold-flow problems of the normal paraffins. Since attempting for significant branching runs the risk of a high degree of undesired cracking, the predominant product in the isomerized effluent 38 is a mono-branched paraffin.

From the isomerization zone 36, the isomerized effluent 38, or if no isomerization zone 36 is utilized, the deoxygenated effluent 28 (or the liquid portion 32 of the deoxygenated effluent 28), is passed to a separation zone 40. The separation zone 40 may include any equipment capable of separating the isomerized effluent 38 into various components. In a preferred embodiment, the separation zone 40 comprises a separation vessel 42 and a fractionation column 44.

In the separation vessel 42, the isomerized effluent 38 will separate into a vapor stream 46 comprising hydrogen, carbon oxides, hydrogen sulfide and other gases, a liquid hydrocarbon stream 48 and, in some instances, a water stream 50. The vapor stream 46 may be treated in a sweetening zone 52 to remove acid gases, and a purified hydrogen stream 54 may be recycled to the deoxygenation zone 22, the isomerization zone 36 or both.

The liquid hydrocarbon stream 48 comprises hydrocarbons useful as diesel boiling range fuel as well as other hydrocarbons such as propane, naphtha/aviation fuel. Accordingly, the liquid hydrocarbon stream 48 may be separated further in the fractionation column 44 into a light hydrocarbon stream 56, comprising for example $C_3$ hydrocarbons, an aviation fuel or naphtha stream 58, comprising $C_4$ to $C_7$ hydrocarbons, and a diesel boiling range fuel 60 comprising $C_8$ to $C_{24}$ normal and mono-branched alkanes.

The partial hydrogenation of triglycerides and FFAs prior to converting triglycerides and FFAs into hydrocarbons will lower the hydrogen demand associated with converting triglycerides and FFAs into hydrocarbons. Lower purity and lower pressure hydrogen may be used. Additionally, by at least partially saturating triglycerides and FFAs, the feed to the deoxygenation reaction will be rich in saturated oils (also saturated fats). This will allow the pre-hydrogenated feedstock to be stored for longer periods of time and shipped to another refinery without as much loss due to oxidation reactions.

EXAMPLES

In order to support the principles of the present invention, different oils samples of castor, soya, and palm stearin were obtained from commercial sources in India. The same sources also provided a corresponding hydrogenated (or saturated) fats produced using the same oil. The details of the various hydrogenation processes were not disclosed.

The metals content of each of the three unsaturated and unsaturated samples was analyzed by Inductively Coupled Plasma—Optical Emission Spectrometry (ASTM Method UOP 389). Selected results of the analysis are shown below in TABLE 1.

TABLE 1

| Metal | Sat. Castor | Unsat. Castor | Sat. Soya | Unsat. Soya | Sat. Palm Stearin | Unsat. Palm Stearin |
|---|---|---|---|---|---|---|
| Ca | 0.62 | 0.80 | 1.2 | 1.1 | 10.00 | 12.20 |
| Fe | <0.09 | <0.09 | 0.33 | 0.11 | 2.90 | 5.00 |
| Na | ND | ND | ND | 1.00 | 10.40 | 1.60 |
| Ni | 1.30 | <0.03 | 0.9 | ND | 3.00 | <0.03 |
| P | 0.20 | 0.58 | 1.4 | 2.50 | 8.80 | 14.50 |
| Total Metals | 2.97 | 2.12 | 4.65 | 5.29 | 38.96 | 40.17 |

From TABLE 1, it should be appreciated that there is no significant difference in the total metals content between an unsaturated oil and corresponding saturated hydrogenated fat. Except for the nickel content, there is a small but significant drop of 1-2 ppm contaminants in these cases. The increase in nickel throughout the samples may be a result of carry-over into the saturated fat from the catalyst. As can be seen in TABLE 1, the partially hydrogenation resulted in a noticeable reduction of phosphorus levels in all cases. As most vegetable oils contain phospholipids, the use of a partial hydrogenation prior to conversion should aide in substantially removing phosphorus from triglycerides and FFAs.

The stoichiometric demand of hydrogen is 0.93 $Nm^3$ for one unit iodine value drop per ton of triglyceride; whereas actual measured consumption has been reported to be up to 1.1 $Nm^3$, especially in older plants. The values of TABLE 2, below, were generated assuming ~1 $Nm^3$ hydrogen per unit iodine value per ton lipid feedstock, and a conversion factor of 0.08988 $Nm^3$/kg for hydrogen was used.

TABLE 2

| # | Parameter | Castor Oil | Soya Oil | Palm Stearin Oil |
|---|---|---|---|---|
| 1 | Iodine value reduction after hydrogenation | 83.46 | 128.38 | 32.41 |
| 2 | Hydrogen demand for deoxygenation, percent of feed, after pre-hydrogenation | 0.75% | 1.15% | 0.29% |
| 3 | Hydrogen demand for deoxygenation, percent of feed, before pre-hydrogenation | 3.25% | 3.05% | 2.60% |
| 4 | Hydrogen deoxygenation demand reduction, % of original chemical H2 consumption (#2 divided by #3) | 23.1% | 37.8% | 11.2% |

Not unsurprisingly, the more unsaturated the feedstock used for pre-hydrogenation, the less chemical hydrogen consumption required after the pre-hydrogenation step. Additionally, for feedstock with a high unsaturation index e.g. soya oil or *jatropha* oil, the pre-hydrogenation may minimize storage-related formation of peroxides and epoxides which can potentially affect catalyst used to convert the fats and oils in the deoxygenation zone.

In sum, the processes described above utilize less high pressure/less high purity hydrogen gas to provide a transportation fuel stream from the renewable feedstocks. Additionally, the pre-hydrogenated feedstock is able to be stored much longer than other feedstocks with lower damage to deoxygenation catalysts. Further, a guard bed used to protect downstream equipment can be smaller and the adsorbent therein may last longer.

It should be appreciated and understood by those of ordinary skill in the art that various other components such as valves, pumps, filters, coolers, etc. were not shown in the drawings as it is believed that the specifics of same are well within the knowledge of those of ordinary skill in the art and a description of same is not necessary for practicing or understating the embodiments of the present invention.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A process for producing a transportation fuel from a renewable feedstock, the process comprising:

pretreating a renewable feedstock to remove contaminants from said renewable feedstock in a first pretreatment zone to provide a pretreated feedstock;

pre-hydrogenating the pretreated feedstock in a pre-hydrogenation zone, the pre-hydrogenation zone comprising at least one reactor having a hydrogenation catalyst and being operated under conditions to partially hydrogenate the pretreated feedstock to provide a pre-hydrogenated feedstock that has at least 50% of phosphorus removed;

removing contaminants from said pre-hydrogenated feedstock;

deoxygenating the pre-hydrogenated feedstock in a deoxygenation zone, the deoxygenation zone comprising at least one reactor having a catalyst capable of deoxygenating the pre-hydrogenated feedstock under deoxygenation conditions and providing a deoxygenated effluent;

separating a liquid portion from said deoxygenated effluent comprising mostly normal paraffins, and separating a gaseous portion from said deoxygenated effluent comprising hydrogen, carbon dioxide, carbon monoxide, water vapor, propane, at least one sulfur component and a phosphorus component;

wherein both the pre-hydrogenation zone and the deoxygenation zone receive a hydrogen gas stream, and wherein the hydrogen gas stream received by the pre-hydrogenation zone has a lower purity, a lower pressure or both compared to the hydrogen gas stream received by the deoxygenation zone and;

isomerizing said liquid portion in an isomerization zone comprising a reactor having a catalyst capable of isomerizing at least a portion of said liquid portion to provide an isomerized effluent;

separating at least one transportation fuel stream from said isomerized effluent.

2. The process of claim 1 and wherein the hydrogen gas stream received by the pre-hydrogenation zone has a lower purity and a lower pressure compared to the hydrogen gas stream received by the deoxygenation zone.

3. The process of claim 1 wherein the pressure of the hydrogen gas stream received by the deoxygenation zone is at least 2 MPa.

4. The process of claim 1 wherein the purity of the hydrogen gas stream received by the deoxygenation zone is at least 90%.

5. The process of claim 1 wherein the reactor in the isomerization zone and the reactor in the deoxygenating zone are the same.

6. The process of claim 1 further comprising:
storing the pre-hydrogenated feedstock in containers.

7. The process of claim 6 further comprising:
transporting the containers of the pre-hydrogenated feedstock to the deoxygenation zone.

8. The process of claim 1 further comprising:
removing contaminants from the pre-hydrogenated feedstock in a guard bed prior to deoxygenating the pre-hydrogenated feedstock in the deoxygenation zone.

9. A process for producing a transportation fuel from a renewable feedstock, the process comprising:
passing a renewable feedstock to a first pretreatment zone, the pretreatment zone comprising at least one reactor configured to degum the renewable feedstock, bleach the renewable feedstock, polish the renewable feedstock or a combination thereof, to provide a pretreated feedstock;

passing the pretreated feedstock to a pre-hydrogenation zone, the pre-hydrogenation zone comprising at least one reactor having a hydrogenation catalyst and being operated under conditions to partially hydrogenate, in the presence of hydrogen, the pretreated feedstock to provide a pre-hydrogenated feedstock that has at least 50% of phosphorus removed;

removing contaminants from said pre-hydrogenated feedstock:

passing a first hydrogen containing gas to the pre-hydrogenation zone, the first hydrogen containing gas having a first pressure and a first purity;

passing the pre-hydrogenated feedstock to a deoxygenation zone, the deoxygenation zone comprising at least one reactor having a catalyst capable of deoxygenating, in the presence of hydrogen, the pre-hydrogenated feedstock under deoxygenation conditions to provide a deoxygenated effluent; and, passing a second hydrogen containing gas to the deoxygenation zone, the second hydrogen containing gas having a second pressure and a second purity;

wherein the second pressure is at least 2 MPa, and wherein at least one of the second pressure and the first pressure and the first purity and the second purity are different, isomerizing the deoxygenated effluent in an isomerization zone, the isomerization zone comprising a reactor having a catalyst capable of isomerizing at least a portion of the deoxygenated effluent to provide a isomerized effluent; and, separating at least one transportation fuel stream from the isomerized effluent.

10. The process of claim 9 further comprising:
separating at least one transportation fuel stream from the deoxygenated effluent.

11. The process of claim 9 wherein the first pressure is lower than the second pressure and wherein the first purity is less that the second purity.

12. The process of claim 11 wherein the second purity is greater than 90%.

13. The process of claim 9 further comprising:
storing the pre-hydrogenated feedstock in one or more containers prior to passing the pre-hydrogenated feedstock to the deoxygenation zone.

14. The process of claim 9 wherein the pre-hydrogenated feedstock is passed to the deoxygenation zone without passing through a guard bed.

15. The process of claim 9 further comprising:
removing contaminants from the pre-hydrogenated feedstock in a guard bed prior to deoxygenating the pre-hydrogenated feedstock in the deoxygenation zone.

16. The process of claim 9 wherein the pre-hydrogenated feedstock is rich in saturated oils.

17. The process of claim 9 further comprising:
passing the deoxygenated effluent to a separation zone having a separation vessel and a fractionation column;
separating the deoxygenated effluent into liquid hydrocarbon stream and a vapor hydrocarbon stream in the separation vessel; and,
separating the liquid hydrocarbon stream into a light hydrocarbon stream, a naphtha stream and a diesel stream.

* * * * *